(12) United States Patent
Westhoff et al.

(10) Patent No.: US 11,534,320 B2
(45) Date of Patent: Dec. 27, 2022

(54) HANDLE FOR A CATHETER AND CORRESPONDING CATHETER

(71) Applicant: BIOTRONIK AG, Buelach (CH)

(72) Inventors: Felix Westhoff, Zurich (CH); Nuria Rothfuchs, Zurich (CH)

(73) Assignee: BIOTRONIK AG, Buelach (CH)

( * ) Notice: Subject to any disclaimer, the term of this patent is extended or adjusted under 35 U.S.C. 154(b) by 447 days.

(21) Appl. No.: 16/499,910

(22) PCT Filed: Apr. 9, 2018

(86) PCT No.: PCT/EP2018/059011
§ 371 (c)(1),
(2) Date: Oct. 1, 2019

(87) PCT Pub. No.: WO2018/206205
PCT Pub. Date: Nov. 15, 2018

(65) Prior Publication Data
US 2020/0113718 A1    Apr. 16, 2020

(30) Foreign Application Priority Data
May 8, 2017   (EP) ..................................... 17169996

(51) Int. Cl.
*A61F 2/95*   (2013.01)
*A61F 2/966*   (2013.01)

(52) U.S. Cl.
CPC ............ *A61F 2/966* (2013.01); *A61F 2/9517* (2020.05)

(58) Field of Classification Search
CPC .......... A61F 2/962; A61F 2/95; A61F 2/9517; A61F 2/966; A61F 2/9522; B23K 26/53;
(Continued)

(56) References Cited

U.S. PATENT DOCUMENTS

2007/0039476 A1   2/2007  Kodden
2009/0270969 A1   10/2009 Fargahi et al.
(Continued)

FOREIGN PATENT DOCUMENTS

DE   19815119 C1   1/2000

OTHER PUBLICATIONS

Musson, Frederique; International Search Report for Application No. PCT/EP2018/059011; dated May 29, 2018.
(Continued)

*Primary Examiner* — Erich G Herbermann
(74) *Attorney, Agent, or Firm* — Greer, Burns & Crain, Ltd.; Steven P. Fallon (57) ABSTRACT

A handle for a catheter having an inner shaft and a retractable shaft. The handle includes a housing, a pull cable and a release button mounted movably on the housing. A sleeve is secured in the housing and a brake hose is guided movably in the longitudinal direction in a continuous opening of the sleeve. The brake hose has a first continuous opening for arrangement of the pull cable and a second continuous opening for arrangement of the inner shaft. The brake hose configured and arranged such that its position relative to the sleeve in a first state is fixed by the release button, and such that the brake hose in a second state is displaceable after actuation of the release button together with the pull cable in the longitudinal direction of the sleeve and relative to the sleeve and the inner shaft in the proximal direction in order to retract the retractable shaft, such that the retractable shaft can be connected to the pull cable.

14 Claims, 6 Drawing Sheets

(58) Field of Classification Search
CPC .... A61B 2017/3445; A61B 2017/3466; A61B 17/3417; A61B 17/2841
See application file for complete search history.

(56) References Cited

U.S. PATENT DOCUMENTS

| | | | |
|---|---|---|---|
| 2010/0004606 A1 | 1/2010 | Hansen et al. | |
| 2010/0286756 A1* | 11/2010 | Dorn | A61M 25/0147 623/1.11 |
| 2014/0358156 A1 | 12/2014 | Argentine | |
| 2016/0074190 A1* | 3/2016 | Cummins | A61F 2/966 623/1.11 |

OTHER PUBLICATIONS

Geuer, Melanie; European Search Report for Application No. 17169996.0 ; dated Sep. 15, 2017.

* cited by examiner

HANDLE FOR A CATHETER AND CORRESPONDING CATHETER

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2018/059011, which was filed Apr. 9, 2018, which application claimed priority from European Application EP 17169996.0, which was filed May 8, 2017.

FIELD OF THE INVENTION

The invention relates to a handle for a catheter having an inner shaft and a retractable shaft, wherein the handle has a housing and a release button mounted movably on the housing.

BACKGROUND

Catheters are generally understood to be tubes or hoses of different diameter made of different materials, by which hollow organs such as the bladder, stomach, intestine, blood vessels or the heart can be probed, emptied, filled, flushed or otherwise treated in a minimally invasive manner. The tubular or hose-like portion of the catheter to be introduced into the body of a human or animal that is to be treated is referred to as a shaft, at the distal end of which there is arranged the catheter tip, which reaches furthest of the catheter elements into the body to be treated. Directional indications, such as distally and proximally, within the scope of this application shall be understood accordingly always within the sense of closer to the catheter tip and closer to the operator, respectively.

Intravascular catheters having an active or passive electrode are known, particularly for use in the cardiothoracic region, and are introduced into main veins or arteries, for example into the femoral vein, and from there can be advanced to different points in the heart or to the coronary vessels. These catheters are used to display or simulate the electrical activity of the heart or to remove regions having abnormal electrical activity. The latter case, known as ablation therapy, is used for example as therapy for cardiac arrhythmia. Furthermore, catheters are also used, for example, to achieve a reduction in blood pressure by neuromodulation of the renal nerves (renal plexus). Further examples of catheters are those that are used for insertion of a stent and/or that have a balloon at their catheter tip which, when dilated, can be used to widen the vessel or expand a stent at the site to be treated. In order to release a device such as a stent, a catheter often has an inner shaft and a retractable shaft surrounding the inner shaft.

The shaft of a catheter of this kind is generally connected at its proximal end to a handle for catheter control and as appropriate fluid supply control. For example, the retractable shaft is retracted by a pull cable using the handle. Handles of known catheters often have the problem that as the pull cable is retracted it winds around the inner shaft of the catheter. The function of the catheter is compromised as a result. Catheter handles in the following example publications can exhibit such compromised function.

Document DE 10 2005 051 469 A1 discloses a device for introducing a self-expanding stent into a bodily vessel, which device, at its proximal end, has a grip with a feedthrough, via which a slide element and a wire guide catheter are secured to the grip, and comprising a lever, which is connected to the grip via a rotational joint. The slide element is used to stabilise the stent as a hose is retracted from the wire guide catheter. A locking button is also provided, which prevents a relative movement between a hose and a slide element. Once the locking button has been released, by actuating the lever, an encasing hose can be retracted over the path of a tooth pitch of a toothed rack with each actuation stroke, said toothed rack also being secured to the grip.

Document DE 198 15 119 C1 discloses a drive device for a resilient probe, in particular a medical probe. The wire-like probe is laid in the drive device through a front opening and lies on a rib. The rib has a curved support surface for improved lateral fixing of the wire probe. The wire probe is then guided out again through a grip of the drive device on the proximal side. A wheel with a circular, peripheral-side conical groove tapering towards the middle is also provided on the drive device, wherein the groove width and the position of slots on the drive device, into which lateral axle pins of the wheel are fitted, are selected such that the probe is pressed against the rib by the groove walls of the wheel and is thus held in the groove in a frictionally engaged manner.

SUMMARY OF THE INVENTION

The invention provides a handle for a catheter which avoids a winding of the pull cable around the inner shaft and improves the handling of the catheter. In a preferred embodiment, a hollow-cylindrical sleeve is secured in the housing of the handle, and a brake hose is guided movably in the longitudinal direction through the continuous opening (lumen) of said sleeve, wherein the brake hose has a first continuous opening (lumen) for arrangement of the pull cable of the handle and a second continuous opening (lumen) for arrangement of the inner shaft of the catheter. The brake hose is configured such that its position relative to the sleeve (and the housing) of the handle in a first state is fixed by the release button, and in that the brake hose in a second state is displaceable, after actuation of the release button, together with the pull cable in the longitudinal direction of the sleeve and relative to the sleeve and the inner shaft in the proximal direction in order to retract the retractable shaft, wherein the retractable shaft can be connected to the pull cable. In the first state, which constitutes the starting state of the release button, the brake hose and the pull cable fixed therein therefore cannot move. The second state of the brake hose occurs when the release button has been actuated and the brake hose has been released hereby.

A continuous opening in a hose, a shaft, or a sleeve is usually also referred to as an (inner) lumen of the hose, the shaft, or the sleeve. This lumen or the continuous opening is an inner cavity, which is surrounded by the hose, the shaft, or the sleeve.

The first and the second continuous opening of the brake hose are arranged adjacently in the brake hose as considered in cross-section. It is therefore clear that the brake hose in one exemplary embodiment has a cross-section deviating from a circular shape. A rotation of the brake hose in the sleeve is hereby hindered.

BRIEF DESCRIPTION OF THE DRAWINGS

Further features and advantages of the present invention and embodiments thereof shall be explained below with reference to the figure and specific examples of the present invention, wherein.

DETAILED DESCRIPTION OF THE PREFERRED EMBODIMENTS

A preferred handle according to the invention also has the advantage that a winding of the pull cable around the inner shaft is prevented due to the arrangement of the pull cable and the inner shaft in separate openings (lumen) of the brake hose. In addition, the inner shaft is guided by the brake hose and the sleeve during the release, for example, of a stent at the distal end of the catheter (catheter tip). This stabilises the inner shaft. The pull cable is preferably formed as a pull wire. The pull cable is fixedly arranged in the first opening of the brake hose and is thus connected to the brake hose.

The sleeve preferably has a length (dimension in the longitudinal direction of the sleeve), which is greater than the length of the implant to be released. This means that the sleeve can protrude beyond the distal end of the handle. For example, the implant can be a self-expanding extent. In systems suitable for a stent up to 200 mm long, the overall length (handle (approximately 150 mm)+sleeve outside the handle (approximately 100 mm)) of the sleeve can be for example 250 mm. An improved guidance of the pull cable and of the catheter shafts and also a stabilisation of the part of the catheter that in use remains outside the patient is hereby achieved.

In one exemplary embodiment the handle has a reel which is secured to the housing and which is mounted rotatably and to which the pull cable is secured and onto which the pull cable (or the pull cable with the brake hose) can be wound in the event of displacement in the proximal direction. Because of the reel, which is accessible from outside through a corresponding opening in the housing of the handle and is rotatable by the user, the pull cable with the brake hose can be easily removed from the sleeve. Since the pull cable is secured to the retractable shaft of the catheter, the retractable shaft is thereby easily displaceable relative to the inner shaft. The reel is preferably arranged at the distal end of the handle so as to be able to be easily operated. The pull cable, which runs in the direction of the proximal end of the handle, and the brake hose are preferably deflected with little friction in the direction of the reel at the proximal end of the handle by means of a deflection rib arranged in the housing in order to be wound up, and therefore the guidance of brake hose and pull cable in the housing of the handle is further improved.

In a further preferred exemplary embodiment, the sleeve has a continuous opening of oval cross-section for arrangement of the brake hose, wherein the large diameter of the oval cross-section extends in the direction of the adjacently arranged first and second openings of the brake hose. The oval opening of the sleeve additionally hinders a rotation of the brake hose in the sleeve, the brake hose not being rotationally symmetrical in cross-section. A transfer of torque from the handle to the hose system of the catheter is also made possible.

It is also advantageous if the position of the brake hose in the first state is fixed via a positive fit or frictional fit between the release button and the brake hose. To this end, the release button for example has a U-shaped portion, preferably with at least one tooth-shaped protrusion arranged on a side face of the U-shaped portion and/or at least one pinching edge. The U-shaped portion preferably has an inner diameter that is smaller than the diameter of the brake hose in the same direction, so that a force which fixes the brake hose in the housing or in the sleeve acts on the brake hose by means of a frictional and/or positive fit, when the brake hose is arranged in the slot.

A particularly effective frictional and/or positive fit can be attained by the release button in the first state when the sleeve has a recess in the region in which the positive fit can be produced between the release button and the brake hose in the first state, in such a way that the brake hose is exposed in the region of the recess. Alternatively, the sleeve can be interrupted in this region. The release button thus acts directly on the brake hose.

In a further exemplary embodiment, the separation (peeling) of the brake hose from the inner shaft of the catheter is improved when a slot that is continuous as far as the second opening is provided in the lateral surface of the brake hose. The slot thus runs radially relative to the brake hose or in respect of the inner shaft. The slot preferably extends along the entire length of the brake hose.

The material of the brake hose preferably contains Teflon and/or another fluoropolymer and/or a thermoplastic compound. Teflon in particular has good sliding properties, such that the retraction of the brake hose in the sleeve and around the deflection rib or the deflection reel can be performed with little application of force and thus precisely.

In a further preferred exemplary embodiment, the release button has a preferably finger-like blocking element, which in the first state blocks rotation of the reel onto which the pull cable is wound in the event of retraction and in the second state allows rotation of the reel. The blocking element is in the first state connected to the reel, for example by a positive fit, whereas this positive fit no longer exists in the second state. For example, a tip that is formed at the end of the blocking element distanced furthest from the release button engages in a toothed wheel provided on the reel next to the housing wall. The movement of the toothed wheel and also of the reel (since the wheel is rigidly connected to the reel) is thereby prevented. In the second state, the engagement of the blocking element in the toothed wheel is cancelled by actuation of the release button, and the toothed wheel and the reel can rotate freely. The handle is thereby protected in an additional way against accidental retraction of the pull cable and thus of the retractable shaft.

In a further exemplary embodiment of the handle according to the invention, the release button has a catch element, which, upon actuation of the release button, engages in a corresponding catch counter element, which is arranged on or secured to the housing. The catch element forms a positive fit with a catch counter element. The catch element forms a positive fit with a catch counter element. The catch element is, for example, formed as a finger-like protrusion, secured to the release button, with a hook at the front end. The catch counter element is a rib, which is mounted on the housing, preferably is formed in one piece with the housing, and which is engaged around by the hook in the second state.

The release button is held in the second state by the catch element and the catch counter element.

It is advantageous for the assembly of the catheter with handle if the release button largely grasps around the sleeve, wherein an opening extending along the longitudinal direction of the sleeve is provided on the release button and is used for the laying of the sleeve with pull cable and inner shaft. Since the sleeve can be placed in the release button instead of being inserted, the assembly time is significantly reduced.

The above problem is also solved by a catheter having a retractable shaft and an inner shaft and an above-described handle, wherein the inner shaft is arranged in the retractable shaft. In addition, an outer shaft can be provided on the catheter. The catheter according to the invention has the advantages described above in relation to the handle.

The above-mentioned advantages are provided in particular for a catheter where a (preferably self-expanding) implant is arranged on the inner shaft and is released by the relative movement of the retractable shaft. Implants of this kind can be heart valve prostheses with a self-expanding main structure, leadless pacemakers (leadless pacer), self-expanding closure systems, and in particular self-expanding stents.

In one exemplary embodiment, the pull cable is secured to the retractable shaft and the inner shaft is secured to the housing of the handle. The retractable shaft can thereby be displaced in the proximal direction by the pull cable. A displacement in the distal direction is also possible when the pull cable is suitably rigid. The pull cable is secured to the retractable shaft preferably by a corresponding sleeve, wherein in the starting state (i.e. prior to actuation of the release button) the location of the fastening is arranged in the sleeve of the handle, more specifically preferably at the distal end of the sleeve.

If the catheter has an outer shaft, this is preferably secured to the sleeve of the handle, more specifically to the distal end thereof, for example is connected to the sleeve in an integrally bonded manner, for example by welding.

The additional outer shaft, also often referred to as a stabiliser shaft, surrounds the retractable shaft and the inner shaft arranged therein over the majority of the length thereof. It is used to improve the insertability into the patient and to stabilise the overall system, in particular during release of the implant.

A simple and economical and reliable method for operating an above-described catheter, for example for releasing a self-expanding stent, includes the steps that the release button is actuated and that the brake hose is then displaced together with the pull cable arranged therein in a longitudinal direction of the sleeve and relative to the sleeve and the inner shaft in a proximal direction. If the handle has a reel connected to the pull cable, the brake hose is displaced relative to the sleeve of the handle in a proximal direction by means of rotation of the reel mounted rotatably on the housing of the handle in order to wind up the pull cable and/or the brake hose. The pull cable is therefore retracted by rotation at the reel. The reel for this purpose for example has a fluting on an outer edge of a rotary wheel rigidly connected to the reel, which fluting facilitates a rotation of the reel. Alternatively or additionally, the reel is made of a soft material (for example a soft plastic), which also ensures greater friction between the reel and pull cable.

Further objectives, features, advantages and possible applications of the invention will become clear from the following description of exemplary embodiments of the invention with reference to the figures. Here, all features described and/or shown in the figures, taken individually or in any combination, form the subject of the present invention, moreover independently of their summary in the individual claims and the dependency references of the claims.

Figure 1:
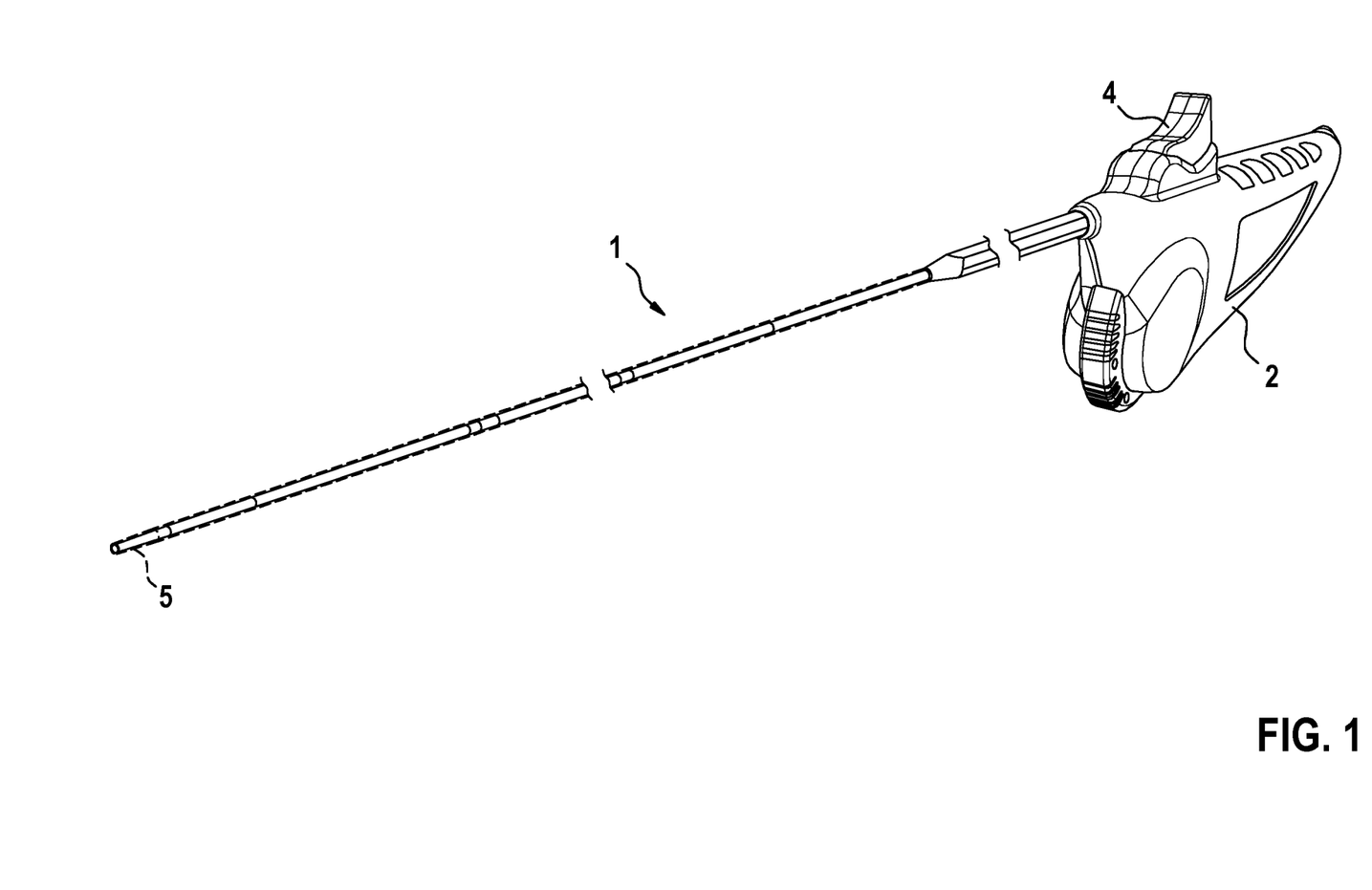
FIG. 1 a catheter with a handle in a view from the side.
Figure 2:
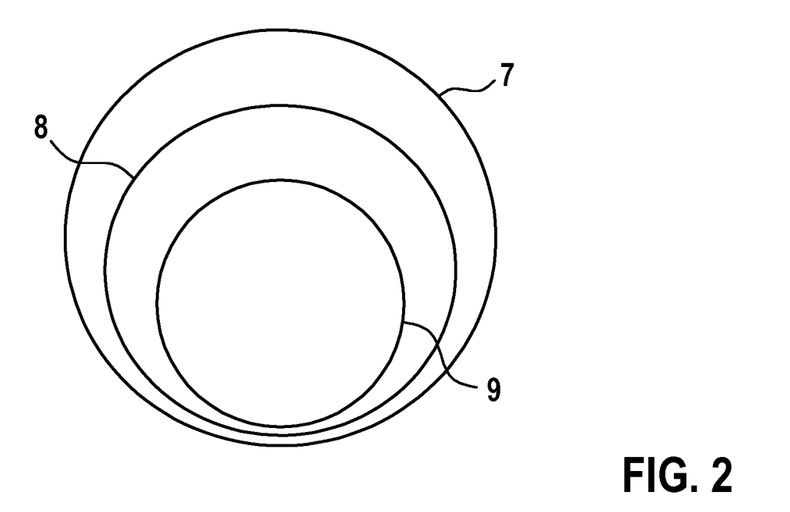
FIG. 2 the shaft of the catheter according to FIG. 1 in a cross-section.

FIG. 1 shows an example of a catheter 1 with a proximally arranged handle 2. The handle 2 has a release button 4. With the handle 2, which can be operated one-handed, an object arranged at the catheter tip 5, i.e. at the outermost distal end of the catheter, for example a self-expanding stent, can be positioned and released. The object is released for example with a triaxial shaft system, which is shown in FIG. 2. The object is released inter alia by actuation of the release button 4, which prevents accidental release.

The triaxial shaft of the catheter 1, consisting of an outer shaft 7, a retractable shaft 8, and an inner shaft 9, is shown in cross-section in FIG. 2. Other shaft designs can also be used with the invention. In FIG. 2, the inner shaft 9 is arranged within the retractable shaft 8, which is disposed within the outer shaft 7. In order to release the inner shaft 9 and therefore the object that is to be introduced (not shown), the retractable shaft 8 is displaced proximally.

The handle 2 according to the invention is shown in detail in FIGS. 3 to 7. This handle from FIGS. 1 and 2 represents an embodiment of the catheter system according to the invention. The housing 11 consists of two halves which can be joined together releasably, wherein only one housing half is visible in FIGS. 3 and 4, wherein the housing halves for example can be fixedly connected to one another by means of a screwed connection. Alternatively, the two halves can also be connected to one another by means of a clamped connection.

Figure 3:
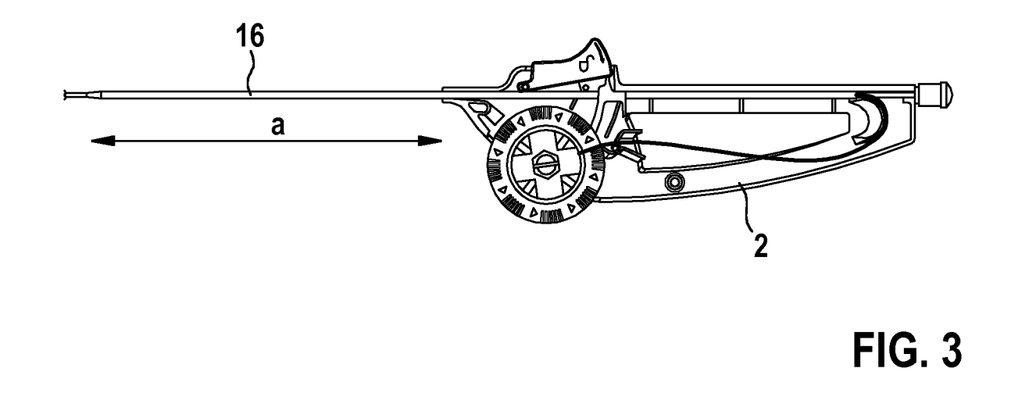
FIG. 3 a handle according to the invention with opened housing.
Figure 4:
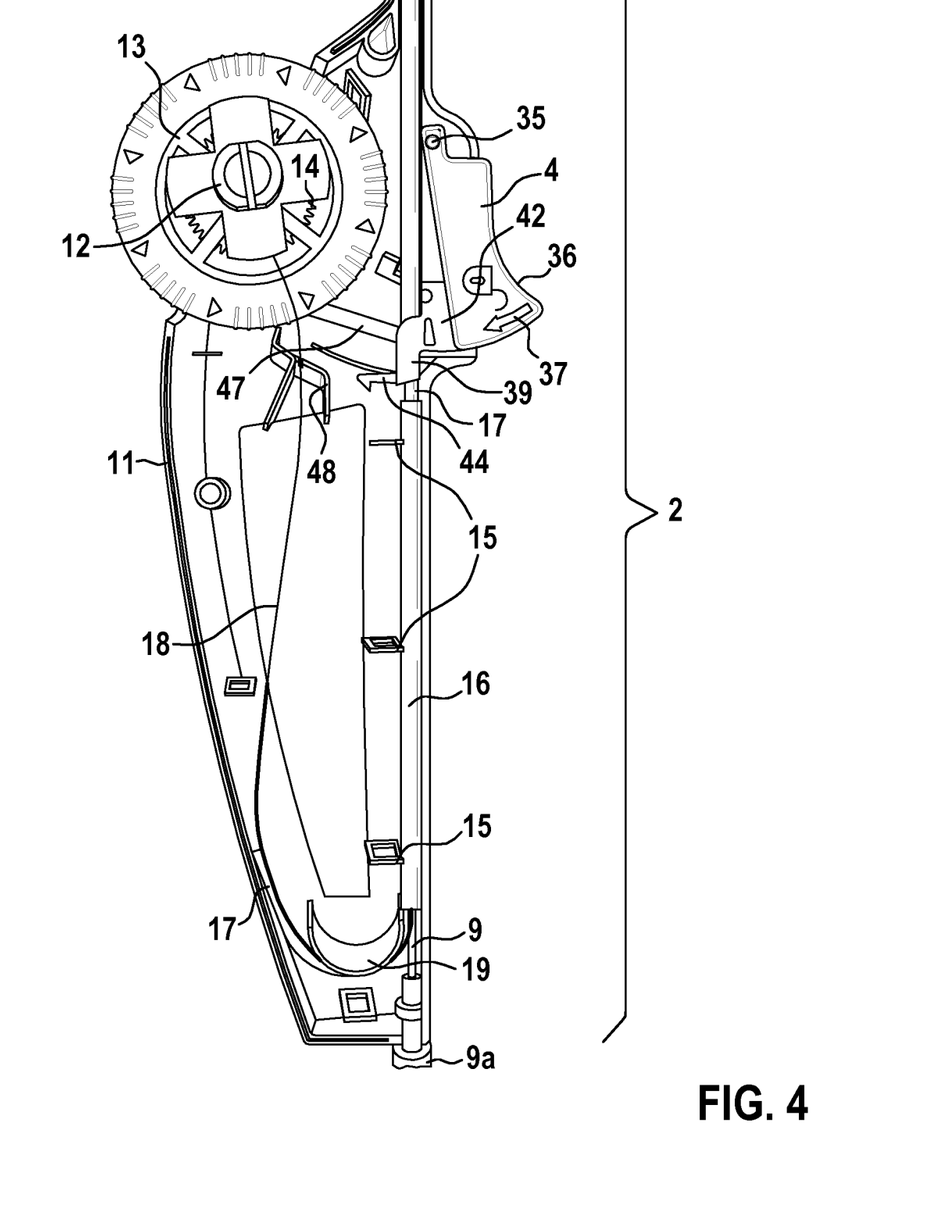
FIG. 4 an enlarged view of the opened housing of the handle according to FIG. 3, FIG. 5 the release button with brake hose of the handle according to FIG. 3 in a perspective view from the side, FIG. 6 the arrangement according to FIG. 5 in a view from the side, and FIG. 7 the sleeve with brake hose, inner shaft, and pull cable of the handle according to FIG. 3 in a cross-section.

A reel 12 for winding up a pull cable 18 (for example embodied as a pull wire) is provided at the proximal end of the housing 11. The reel 12 is secured to the housing in a rotatably mounted manner and is rigidly connected to a wheel 13, by means of which a user can rotate the reel 12. To this end, the wheel 13 on its outer periphery has a suitable fluting and arrows, which indicate the correct direction of rotation in order to wind up the pull cable 18. The reel-side end of the pull cable 18 is fixedly connected to the reel 12. A toothed wheel 14 is also fixedly connected to the reel 12 and is arranged between the wheel 13 for rotation by the user and the housing 11. The toothed wheel 14 is formed in such a way that it is rotatable only in one direction.

After a few revolutions of the wheel 13, not only is the pull cable 18 wound onto the reel 12, but also the combination of pull cable 18 and brake hose 17. This is accompanied by a corresponding increase of the amount of material to be received by the reel 12. Here, the reel 12 is advantageously conical. There are a number of possibilities for the specific embodiment of the reel, these being described in EP 2 111 826, the content of which is hereby incorporated by reference.

Transverse struts 15 are additionally provided on the inner side of the housing 11 and fix a sleeve 16 to the housing 11. As is shown in FIG. 3, the sleeve 16 protrudes by a length a beyond the proximal end of the housing 11 of the handle 2. An additional guidance of the catheter shaft as the pull cable 18 is retracted is hereby achieved.

Figure 7:
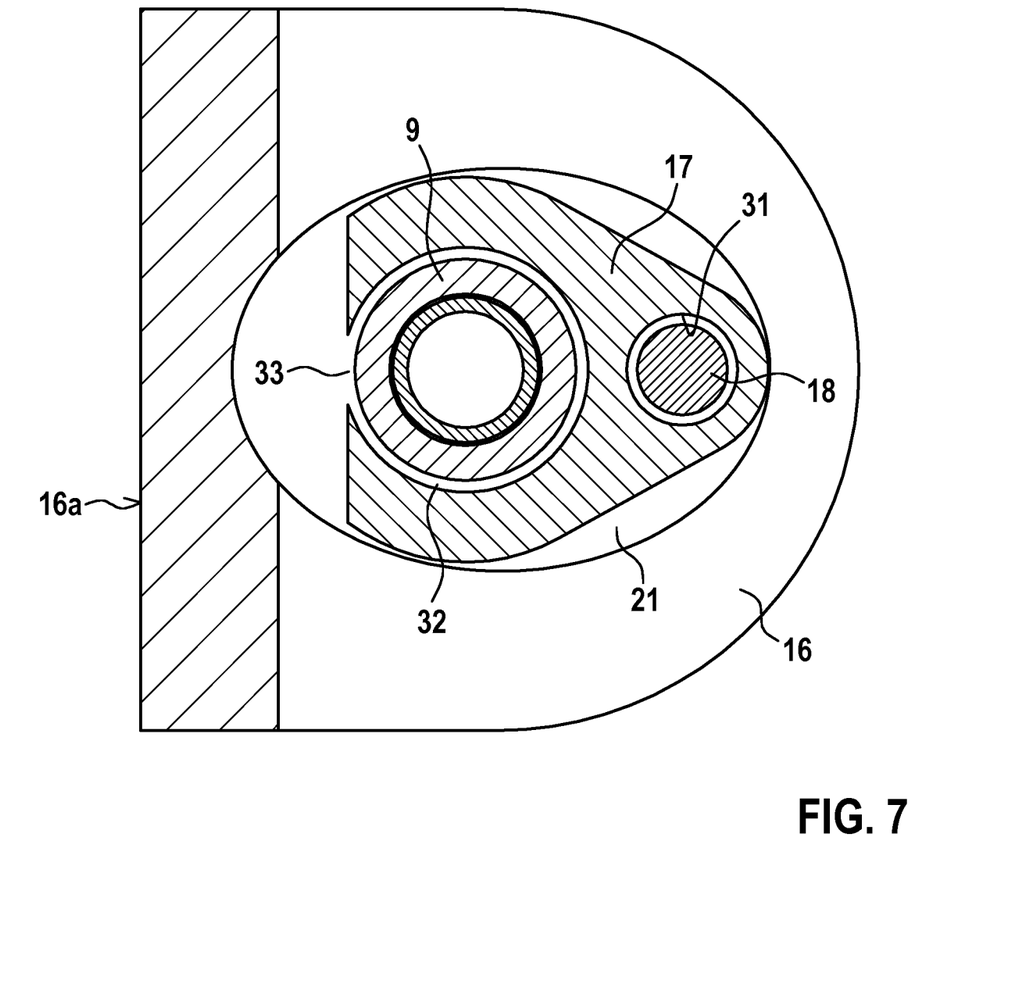

The sleeve 16 can be seen in cross-section in FIG. 7. The sleeve 16 has an oval continuous opening (lumen) 21 for receiving a brake hose 17. The sleeve 16 is rounded in cross-section on an outer side, whereas a straight contact face 16a for bearing against the housing 11 is provided on the opposite side.

The brake hose 17 has a smaller continuous first opening 31 for the arrangement of the pull cable 18 and a larger second opening 32, provided with a slot 33, for receiving the inner shaft 9 disposed in the second opening 32. On account of the arrangement of the openings 31, 32 adjacently in the brake hose 17, a non-rotationally symmetrical form is provided for the brake hose 17.

The slotted opening 32 of the brake hose 17 enables a simple attachment to and release from the inner shaft 9. The inner shaft 9 is guided along the entire sleeve 16 by the brake hose 17, so that it cannot escape under pressure. Merely at the proximal end of the inner shaft 9 does the inner shaft 9 protrude from the sleeve 16. At the proximal end, the inner shaft 9 has a fluid connector 9a for flushing the continuous opening of the inner shaft (inner lumen). The continuous opening of the inner shaft is used to receive a guide wire, which is likewise guided proximally from the inner shaft (not shown in detail). In this region, as the pull cable 18 is retracted with the brake hose 17, the brake hose 17 is automatically removed (peeled) from the inner shaft 9, and this can be implemented in a simple manner on account of the slot 33. The automatic removal of the brake hose 17 from the inner shaft is implemented in that the brake hose 17 is guided around a deflection rib 19, which is provided at the proximal end in the housing 11.

The non-rotationally symmetrical form of the brake hose 17, in combination with the oval opening 21 of the sleeve 16, means that the brake hose 17 cannot rotate in the sleeve 16. As a result of this and on account of the separate guidance of pull wire 18 and inner shaft 9 in separate openings 31, 32, the pull wire 18 is prevented from looping around the inner shaft 9.

Within the housing 11, the brake hose 17 is guided primarily by the sleeve 16 in the oval opening 21 (see FIG. 7). In order to minimise friction, the brake hose 17 is made of a low-friction material, for example Teflon. The sleeve 16 in the region of a U-shaped portion 39 of the release button 4 has a recess or is interrupted there, as can be seen in FIG. 4. The brake hose 17 is thus exposed in this region, such that direct cooperation of the brake hose 17 and the release button 4 is made possible.

Figure 5:
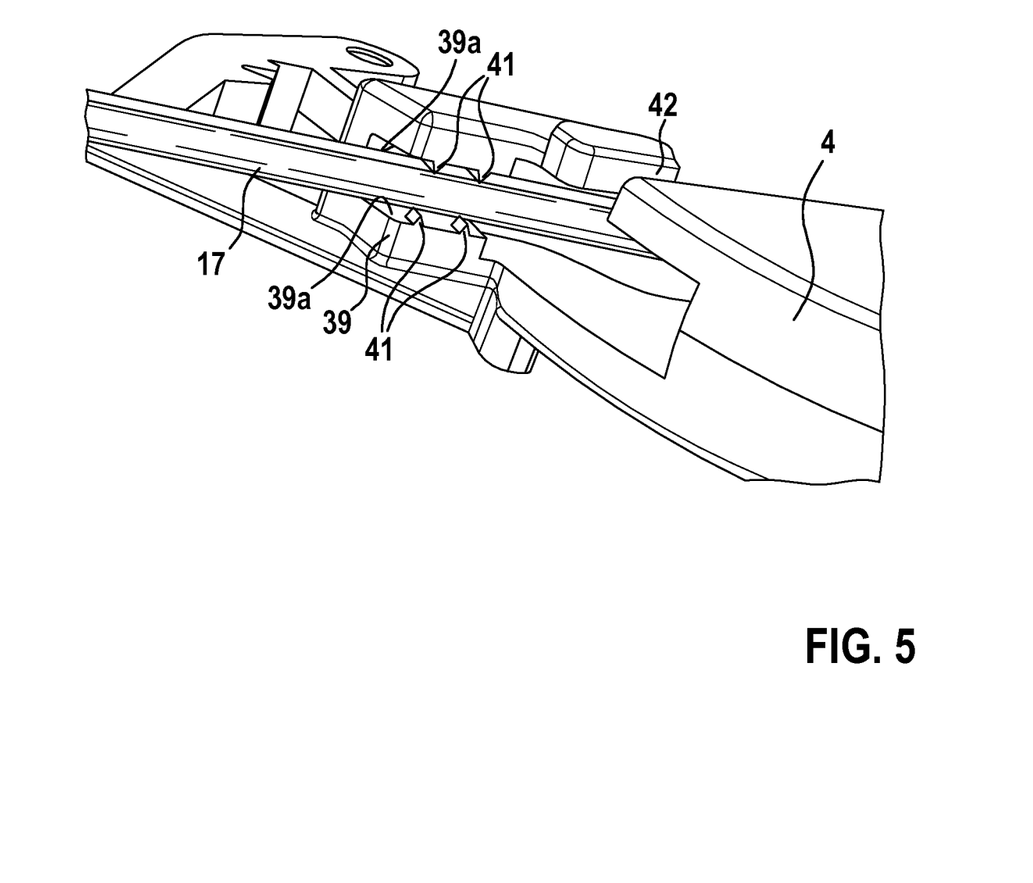
Figure 6:
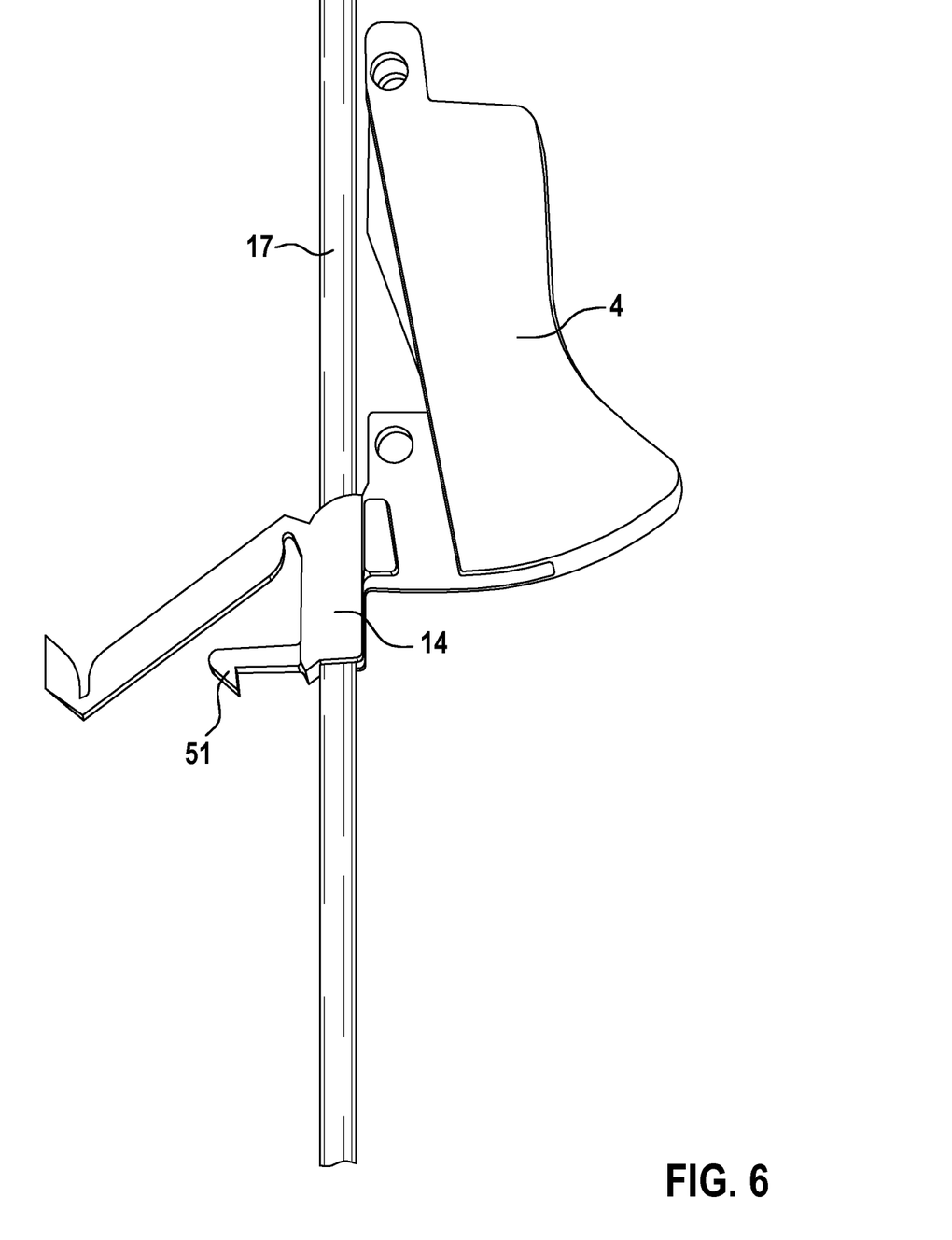

The release button 4 is shown in greater detail merely with the brake hose 17 in FIGS. 5 and 6. The sleeve 16 has been omitted. The release button 4 has substantially a rotated L-shaped and is secured on the housing 11 such that it can pivot about a pin 35 protruding inwardly from the housing 11. On the upper side, on the long limb of the "L", the release button 4 has a depression 36, in which the user can place a finger in order to actuate the release button 4 by pressing down (in the direction of the arrow 37 on the release button 4). In the region of the sleeve 16 or the brake hose 17, the release button 4 forms a U-shaped portion, which engages around the sleeve 16 or the brake hose 17. Two pinching edges 41 are formed on each of the inner side faces 39a of the U-shaped portion 39 and in a first state form a positive and frictional fit with the brake hose 17 and fix the brake hose 17 relative to the housing 11, so that the brake hose cannot move.

A lateral recess 42 in which the brake hose 17 or the sleeve 16 can be placed is also provided on the release button 4. The release button 4 also has, beneath the U-shaped portion 39, a catch element in the form of a hook 44 and a finger-like blocking element 47.

In a first state (starting state, release button 4 in the upper position), the pinching edges 41 form a fictional and positive fit between the release button 4 and the brake hose 17. This generates the braking effect and fixes the brake hose relative to the housing 11 and the sleeve 16. Accordingly, the pull cable 18, which is arranged fixedly in the brake hose 17, is also fixed and retraction of the pull cable 18 is not possible. In the first state, the finger-like blocking element 47 also engages by means of its front end in the toothed wheel 14, so that the toothed wheel 14 and thus reel 12 and wheel 13 cannot be rotated.

If the release button 4 is brought into the lower position by pressing in the direction of the arrow 37, the "brake" is released and the frictional and positive fit between the pinching edges 41 and the brake hose 17 is cancelled. The release button 4 is now in the second state, in which the brake hose 17 is displaceable in the sleeve 16. In this state the object at the catheter tip 5, for example a stent, can be released in that the pull cable 18 is retracted by rotation of the wheel 13. At the end of the actuation movement of the release button 14, the hook 44 engages behind a catch counter element (rib 48 on the housing 11). The release button 4 is hereby fixed in the second state, and a free displacement of the brake hose 17 in the sleeve 16 continually ensured. Upon actuation of the release button 4, the blocking element 47 is also moved, for example by bending at a joint, so that the blocking element 47 is no longer engaged with the toothed wheel 14 and thus releases it. The elements (reel 12 and wheel 13) fixedly connected to the toothed wheel 14 can hereby be rotated, so that the pull cable 18 connected to the reel 12 can be retracted.

In order to prevent an axial displacement of pull cable 16 and brake hose 17, a cylindrical cover can be pressed onto the brake hose 17 optionally directly proximally of the point of the positive and fictional fit between the brake hose and "brake". In this optional embodiment of the invention, the static friction between the brake hose 17 and pull cable 18 is thus increased.

Since the pull cable 18 is connected in the distal region of the sleeve 16 to the retractable shaft 8 of the catheter, the retractable shaft 8 is also retracted via the pull cable 18 by rotation of the wheel 13. The inner shaft 9 remains fixed in the housing 11, and the outer shaft 7 is secured in the distal region of the sleeve 16. Since the sleeve 16 is also fixed in relation to the housing 11, the outer shaft 7 is also not moved when the pull cable 18 is retracted. All three shafts are guided at least into the distal region of the sleeve 16, but merely the inner shaft 9 passes through the sleeve 16 over its entire length.

The catheter 1 according to the invention with the handle 2 according to the invention allows a reliable retraction of the retractable shaft 8 by the pull cable 18 and avoids a winding of the pull cable 18 around the inner shaft 9. The handle 2 additionally allows a transfer of torque from the handle 2 to the shafts 7 to 9.

LIST OF REFERENCE SIGNS 1 catheter
2 handle
4 release button
5 catheter tip
7 outer shaft
8 retractable shaft
9 inner shaft
9a stopper
11 housing
12 reel
13 wheel
14 toothed wheel
15 struts
16 sleeve
16a contact face of the sleeve 16

17 brake hose
18 pull cable
19 deflection rib
21 continuous opening (lumen) of the sleeve 16
31 first opening for the pull wire 18
32 second opening for the inner shaft 9
33 slot
35 pin
36 depression
37 arrow
39 U-shaped portion
39a inner side face of the U shape
a a length of the sleeve 16 outside the housing 11 of the handle 2
41 pinching edge
42 recess
44 hook
47 blocking element
48 rib

The invention claimed is:

1. A handle for a catheter having an inner shaft and a retractable shaft, wherein the handle comprises a housing, a pull cable and a release button mounted movably on the housing, wherein the housing comprises a sleeve having a continuous opening, in which is secured a brake hose guided movably in a longitudinal direction of the sleeve, wherein the brake hose has a first continuous opening for arrangement of the pull cable and a second continuous opening for arrangement of the inner shaft, wherein the brake hose is configured and arranged such that its position relative to the sleeve in a first state is fixed by the release button, and a second state is displaceable, after actuation of the release button, together with the pull cable in the longitudinal direction of the sleeve and relative to the sleeve and the inner shaft in a proximal direction in order to retract the retractable shaft, whereby the retractable shaft can be connected to the pull cable.

2. The handle according to claim 1, wherein the handle has a reel which is rotatably mounted on the housing and on which the pull cable is secured and onto which the pull cable with the brake hose can be wound in the event of displacement in the proximal direction.

3. The handle according to claim 2, wherein the release button comprises a finger-like blocker, which in the first state blocks rotation of the reel and in the second state allows rotation of the reel.

4. The handle according to claim 1, wherein the sleeve (has a continuous opening that is oval in cross-section for arrangement of the brake hose.

5. The handle according to claim 1, wherein the position of the brake hose is fixed in the first state by a positive and/or frictional fit between the release button and the brake hose.

6. The handle according to claim 5, wherein the sleeve comprises a recess, defined in such a way that the brake hose is exposed in the recess.

7. The handle according to claim 1, wherein the brake hose has, in its lateral surface, a slot running continuously as far as the second opening.

8. The handle according to claim 1, wherein a material of the brake hose comprises Teflon.

9. The handle according to claim 1, wherein the release button comprises a catch, which, upon actuation of the release button, engages in a corresponding catch counter, which is arranged on or secured to the housing.

10. The handle according to claim 1, wherein the release button largely grasps around the sleeve, wherein an opening extending along the longitudinal direction of the sleeve is provided on the release button and is used for the laying of the sleeve with pull cable and inner shaft.

11. A catheter having a retractable shaft and an inner shaft and a handle according to claim 1, wherein the inner shaft is arranged in the retractable shaft.

12. The catheter according to claim 11, wherein the pull cable is secured to the retractable shaft and the inner shaft is secured to the housing of the handle.

13. A method for operating a catheter claim 11, wherein the release button is actuated and the brake hose together with the pull cable arranged therein is then displaceable in a longitudinal direction of the sleeve and relative to the sleeve and the inner shaft in the proximal direction.

14. The method according to claim 13, wherein, in order to displace the brake hose relative to the sleeve in the proximal direction, a reel mounted rotatably on the housing of the handle is rotated in order to wind up the pull cable and/or the brake hose.

* * * * *